United States Patent [19]

Wang et al.

[11] Patent Number: 4,831,161

[45] Date of Patent: May 16, 1989

[54] N-(AMIDOALKYL)HYDANTOINS

[75] Inventors: Pen-Chung Wang; Steven P. Crain, both of Midland, Mich.

[73] Assignee: The Dow Chemical Company, Midland, Mich.

[21] Appl. No.: 65,740

[22] Filed: Jun. 24, 1987

Related U.S. Application Data

[62] Division of Ser. No. 774,220, Sep. 9, 1985, Pat. No. 4,692,533.

[51] Int. Cl.$^4$ ............................................. C07D 233/72
[52] U.S. Cl. ................................... 548/312; 540/202; 540/356; 540/454; 540/488; 540/526; 540/563; 544/3; 544/248; 544/253; 544/285; 546/243; 548/213; 548/214; 548/546
[58] Field of Search ............... 548/312, 213, 546, 214; 546/243; 540/526, 488, 563, 454, 356, 202; 544/285, 3, 253, 248

[56] References Cited

U.S. PATENT DOCUMENTS 4,691,021 9/1987 Wang et al. .................... 548/312 X

OTHER PUBLICATIONS

Loudon, G., *Organic Chemistry*, Addison Wesley, Reading, Ma., 1984, pp. 1070–1071, 1181–1186.
Fazio, M., *J. Org. Chem.*, 49, 4889 (1984).
Lee, H. et al., *Handbook of Epoxy Resins*, McGraw Hill, New York, 1967, pp. 5–9 to 5–13.
*Chemical Abstracts*, 67:54074 d (1967) [Shafer, J. et al., *J. Med. Chem.* 10(4), 739–40 (1967)].

*Primary Examiner*—Richard A. Schwartz

[57] ABSTRACT

Prepare N-(amidoalkyl)imides by contacting an imide with a 2-oxazoline under reaction conditions, optionally in the presence of a solvent.

2 Claims, No Drawings

N-(AMIDOALKYL)HYDANTOINS

CROSS-REFERENCE TO RELATED APPLICATION

This is a divisional of application Ser. No. 774,220 filed Sept. 9, 1985, now U.S. Pat. No. 4,692,533.

Background of the Invention

The present invention relates to the aminoalkylation of imides and sulfonamides.

It is known to prepare N-substituted imides. U.S. Pat. No. 4,465,830 teaches the preparation of N,N'-disubstituted hydantoins by reacting hydantoins with hydrazine hydrate and acrylic esters.

It is known to prepare N-substituted imides and sulfonamides using alkylation techniques. For example, U.S. Pat. No. 3,917,636 discloses a process for the preparation of certain N-substituted imides or sulfonamides by contacting an alkali metal salt of the sulfonamide or imide with a substituted ethyl imidazole. The imidazole compound is halogenated or is prepared from a halogenated compound. U.S. Pat. No. 4,110,536 discloses substitution at the imide nitrogen of various 5-(indol-3-yl) hydantoins by halogenating said hydantoin and reacting the halogenated compound with an alkali metal alkoxide in a polar solvent at reflux. Thus, these methods require halogens and alkali metals.

U.S. Pat. No. 4,073,927 teaches the preparation of N,N'-disubstituted hydantoins by reacting a hydantoin with acrylonitrile in the presence of an alkali metal hydroxide.

It would be desirable to have a simple method for the preparation of mono-N-substituted imides and sulfonamides without need of an alkali metal.

SUMMARY OF THE INVENTION

The present invention is such a process comprising contacting an imide or sulfonamide with a 2-oxazoline under reaction conditions such that there is formed a corresponding N-(amidoalkyl)imide. The reaction proceeds smoothly to give a high yield without need of alkali metal, catalyst or solvent, although the latter two optionally can be employed. The N-(amidoalkyl)imides of the present invention are novel chemical intermediates for valuable organic compounds.

DETAILED DESCRIPTION OF THE INVENTION

The process of the present invention advantageously employs a 2-oxazoline and an imide or sulfonamide. The monoimide or sulfonamide reactants desirably employed in the process of the present invention are represented generally by the formula:

Y'''-Z-NH-Z'-Y'' wherein Z is carbonyl or sulfonyl; Z' is carbonyl when Z is carbonyl, otherwise Z' is carbonyl or a bond; and each Y'' independently is a moiety which does not prevent or substantially interfere with the desired reaction. When Z is carbonyl, the imido reactant is an imide, and when Z is sulfonyl, the imide reactant is a sulfonamide. Preferably, each Y'' independently is H or hydrocarbyl of up to about 28 carbon atoms, and can be cyclic or noncyclic, aromatic, aliphatic or mixed aromatic-aliphatic, and can contain heteroatoms. More preferably, each Y'' independently is alkyl, alkenyl, or aryl of up to about 10 carbon atoms. Examples of typical sulfonamides desirably employed in the present invention include, e.g., saccharin (benzoylsulfonic imide; o-benzosulfimide), benzene sulfonamide, N-methyl benzene sulfonamide, toluene sulfonamide, and methyl sulfonamide. Most preferably, cyclic imides are employed, as when each Y'' combines to form one moiety which is designated Y, as in the following formula depicting preferred cyclic imides:

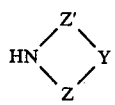

wherein Z and Z' are as previously described; Y is hydrocarbylene, such as alkylene, alkenylene, cycloalkylene, cycloalkenylene and arylene; or —NH—O— wherein O is selected from the group consisting of phenylene, cycloalkylidene, adamantylidene and =C—R'R'' wherein R' and R'' are each independently H, lower alkyl or phenyl.

The alkylene and alkenylene radicals referred to above preferably contain from 2 to 5 carbon atoms. In these radicals, at least two carbon atoms separate the free valences. Preferably, 2 to 3 carbon atoms separate the free valences so that when the radicals are combined with the imide structure a 5- or 6-membered ring results. Some examples of alkylene and alkenylene groups are ethylene, trimethylene, and vinylene. Thus, when Z is carbonyl and Y is each of the aforementioned groups, the imides involved are succinimide, glutarimide, and maleimide, respectively. The indicated imides can further contain one or more alkyl substituents to give structures such as 2-methylsuccinimide and 3,3-dimethylglutarimide. The alkyl substituents can further be combined to give a spiro imide structure. An example of this type of structure is 1,1-cyclohexanediacetimide.

The cycloalkylene and cycloalkenylene radicals preferably contain 5 to 7 carbon atoms in the ring with the free valences on adjacent carbon atoms. Examples of such groups are 1,2-cyclohexylene and 4,5-cyclohexenylene.

When Y is arylene, radicals having two free aromatic valences are involved. Examples of Y thus are phenylene and naphthylene. Examples of imides involved are phthalimide, naphthalimide, 1,2-naphthalenedicarboximide, and 2,3-naphthalene-dicarboximide. The benzene and naphthalene rings in the aforementioned imides can further be substituted with one or more alkyl groups such as methyl, with one or more halogen atoms such as chlorine, or with nitro. Y can further represent pyridinediyl so that derivatives of quinolinimide are involved. When Y in the above structure is phenylene, Z' can be carbonyl and Z can be sulfonyl to give derivatives of o-sulfobenzimide (saccharin).

When Y in the above formula is

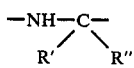

and Z is carbonyl, then

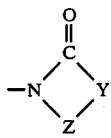

is a hydantoin. Preferred R' and R" substituents are H, lower alkyl radicals containing up to 6 carbon atoms, and phenyl. Examples of such lower alkyl radicals are methyl, ethyl and propyl. Examples of substituted hydantoins include 5,5-dimethylhydantoin, 5-methylhydantoin, 5,5-diethylhydantoin, and 5,5-diphenylhydantoin. When R' and R" are combined, =CR'R" is a cycloalkylidene group and spirohydantoins are involved. The cycloalkylidene groups preferably contain 5 to 7 carbon atoms in the ring and can be exemplified by cycloheptylidene. A more complex ring structure is also possible, such as when =CR'R" is adamantylidene.

For the purposes of the present invention, the term "hydrocarbyl" includes inertly-substituted hydrocarbyl moieties. This also applies to the terms such as alkyl, alkylidene, phenyl, arylene and the like as used herein. For the purposes of the present invention, the term "inert" refers to inertness of a moiety under reaction conditions with respect to the reactive sites of the reactants. For example, 5,5-di(chloromethyl) hydantoin is an imido reactant bearing 2 hydrocarbyl moieties.

Diimido reactants can be employed in conjunction with mono- or bis-(2-oxazolines) to form dimers, oligomers or polymers. Preferred diimido reactants are represented by the formula:

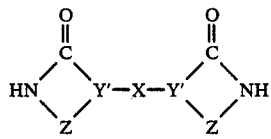

wherein Z is as described hereinabove, X is a polyvalent bridging moiety, and each Y' independently is identical to Y except that Y' is bonded to X. Typically, X is a di-, tri- or tetravalent aliphatic, aromatic, or mixed aromatic aliphatic moiety and can contain heteroatoms such as, for example, nitrogen and oxygen. Examples of preferred X bridging moieties include alkylene, alkenylene, cycloalkylene, cycloalkenylene, arylene, alkanediylidene, alkanetetrayl, and the like, typically of up to about 28 carbon atoms, and preferably of from about 1 to about 10 carbon atoms. For example, the X moiety is methylene in 1,1'-methylene-bis-(5,5'-dimethylhydantoin). The moiety X can consist of two moieties which, when taken together, form a cyclic bridge including the atoms of the Y' moiety. The cyclic bridge can, of course, be carbocyclic or heterocyclic, saturated or unsaturated, alicyclic or aromatic. A preferred example of a cyclic-bridged diimido reactant is pyromellitic diimide. Various mono- and bis-hydantoins and cyclic imides are taught in the following references: U.S. Pat. Nos. 3,542,803; 3,635,844; 3,635,845; 3,640,910; 3,697,539; 3,725,342; 3,793,248; 3,821,243; 3,839,298; 3,907,719; 3,963,607; 4,143,188; 4,140,658; 4,210,744; 4,448,942; and 4,486,443. The teachings of these references is incorporated herein by reference to the extent that they teach imides having a hydrogen atom bonded to at least one imide nitrogen.

A 2-oxazoline is desirably employed in the present invention. The 2-oxazolines are well-known. The following references and references cited therein teach 2-oxazoline compounds and methods for their preparation: U.S. Pat. Nos. 3,716,520; 3,741,944; 3,753,947; 4,024,184; 4,086,273; 4,086,274; 4,200,903; 4,251,459; and 4,326,067. The teachings of all of said references are incorporated herein by reference. Preferred 2-oxazolines employed in the present process are represented generally by the formula:

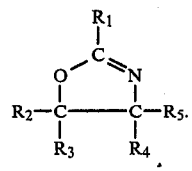

$R_1$ is H, hydrocarbyl, or hydrocarbyl which contains heteroatoms, and typically has up to about 25 carbon atoms.

$R_1$ can also represent a link to a second oxazoline ring to form a bis-oxazoline as exemplified by the preferred structure:

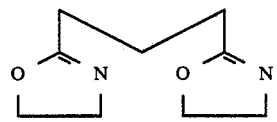

which is disclosed in U.S. Pat. Nos. 2,569,428 and 3,419,520 which are hereby incorporated by reference.

A key aspect is that $R_1$ is inert when it is exposed to other reactants under the reaction conditions. For example, $R_1$ can be hydrogen, methyl, ethyl, undecyl, stearyl, phenyl, benzyl, hydroxyethyl, or p-nitrophenyl. Inert substituents include, for example, the radicals capable of being $R_1$, ethers, thioethers, amides, hydroxy and tertiary amines. $R_1$ is preferably a straight-chain aliphatic radical of 1 to 12 carbon atoms. $R_1$ is most preferably ethyl. $R_2$-$R_6$ which can be the same or different, have the same definition as $R_1$ except that the most preferred embodiment is hydrogen.

An inert solvent is optionally employed in the process of the present invention, although it is preferred to operate in the substantial absence of a solvent. Examples of inert solvents include toluene, ethers, and chlorobenzene.

The process can be conducted at any combination of temperature and pressure at which the reaction proceeds. Ambient pressure preferably is employed for the sake of convenience, although sub-or superatmospheric pressure can be employed if desired. Typically, the process is conducted at a temperature of from about 90° C. to about 150° C., preferably from about 100° C. to about 130° C. Most preferably, the reaction is conducted at reflux.

A catalyst is not required by the process of the present invention. A catalyst can be employed if desired. Most preferably, the process is conducted in the substantial absence of a catalyst. Examples of typical catalysts include protonic acids having non-nucleophilic counterions, onium salts, such as ammonium and phosphonium salts, and Lewis acids. If employed, the catalyst is employed in a catalytic amount. Typically, less than about 5 mole percent of the catalyst, per mole of oxazoline, is employed. Preferably, less than about 2 mole percent of the catalyst is employed.

Lewis acids are well-known to those skilled in the art and are generally defined as a substance that can take up an electron pair to form a covalent bond. Representative examples include $BF_3$, $AlCl_3$, $SnCl_4$, $ZnCl_2$, $FeCl_2$, $h_2WO_3$, $Fe_2SO_4$, $Zn(O_2CCH_3)_2$, $CdCl_2$, $CoCl_2$, and $I_2$.

Protonic acids with non-nucleophilic counterions or anions are also a known class of compounds. Protonic acids contain hydrogen. Representative examples include p-toluenesulfonic acid, sulfuric acid and phosphoric acid. The preferred catalysts are Lewis acids. The most preferred catalyst is zinc acetate. Most preferably, the reaction is carried out in the substantial absence of alkali metals.

When an imide and a 2-oxazoline are contacted as described herein, a corresponding novel N-(amidoalkyl-)imide is formed. The exact structure of the product imide is a function of the reactants and stoichiometry employed. For example, a diimido reactant can be reacted with 2 moles of oxazoline, or vice versa. Additionally, a diimido reactant can be contacted with a bis-oxazoline to form a polymer. In the simplest case, a monoimide is contacted with a mono-oxazoline. It is preferred to employ the oxazoline and the imido reactant in the stoichiometric amounts required to obtain the desired imide product. Nonstoichiometric amounts can be employed if desired. The reaction of a monoimido reactant with a mono-oxazoline is exemplified as follows:

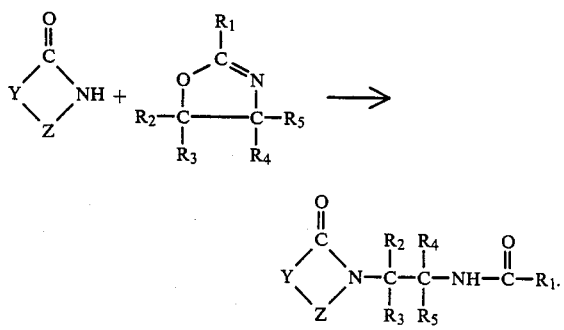

Preferably, the yield in such a reaction is at least about 70 mole percent, more preferably at least about 85 mole percent, and most preferably at least about 90 mole percent. Similarly, the reaction of a diimido reactant with a bis-oxazoline is exemplified as follows:

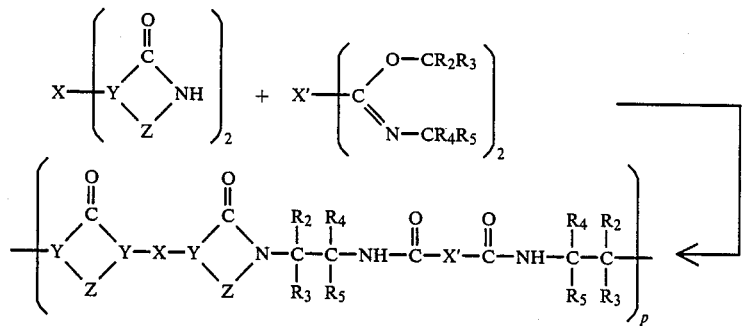

wherein p is at least one, and wherein X' is a bridging moiety defined as the divalent subset of bridging moiety X, with the proviso that X' can be the same as or different than X. By representing imido-reactant moieties as A, and remnants of oxazoline as B, for the purposes of illustration, the following types of products of the present process can be prepared; BAAB, AB, ABBA, and $(AABB)_p$ wherein p is as defined hereinabove.

SPECIFIC EMBODIMENTS

The following examples are given to illustrate the invention and should not be construed as limiting its scope. All parts and percentages are by weight unless otherwise indicated.

EXAMPLE 1

A mixture of 0.1 mole (12.8 g) of 5,5'-dimethylhydantoin and 0.1 mole (9.9 g) of 2-ethyloxazoline is placed in a 100-ml round-bottom flask equipped with a condensing means, a heating means, and a stirring means. The mixture is heated with stirring to 130° C. The progress of the reaction is monitored by proton nuclear magnetic resonance spectroscopy or gas-liquid chromatography, and the reaction time is about 6 hours. The product is isolated by recrystallization from a mixture of ethyl acetate and methanol, and its structure is confirmed by nuclear magnetic resonance spectral data and elemental analysis. The product and its yield are listed in Table I.

EXAMPLES 2-8

The procedure of Example 1 is repeated using the same stoichiometric ratio of reactants except that for each example at least one different reactant is employed. The results are summarized in Table I.

EXAMPLE 9

The procedure of Example 1 is repeated using a different hydantoin and twice as much of the oxazoline. The results are summarized in Table I.

TABLE I

| Example | Imide | Oxazolines | Products | % Yield based on Imide |
|---|---|---|---|---|
| 1 | 5,5'-dimethylhydantoin | 2-ethyloxazoline | [structure: hydantoin-N-CH2CH2-NH-C(O)-Et] | 90 |
| 2 | 5,5'-dimethylhydantoin | 2-methyloxazoline | [structure: hydantoin-N-CH2CH2-NH-C(O)-CH3] | 87 |
| 3 | 5,5'-dimethylhydantoin | 2-phenyloxazoline | [structure: hydantoin-N-CH2CH2-NH-C(O)-Ph] | 85 |
| 4 | succinimide | 2-ethyloxazoline | [structure: succinimide-N-CH2CH2-NH-C(O)-Et] | 86 |
| 5 | succinimide | 2-methyloxazoline | [structure: succinimide-N-CH2CH2-NH-C(O)-CH3] | 92 |
| 6 | succinimide | 2-phenyloxazoline | [structure: succinimide-N-CH2CH2-NH-C(O)-Ph] | 85 |
| 7 | phthalimide | 2-ethyloxazoline | [structure: phthalimide-N-CH2CH2-NH-C(O)-Et] | 80 |
| 8 | 1,2,3,6-tetrahydrophthalimide | 2-ethyloxazoline | [structure: tetrahydrophthalimide-N-CH2CH2-NH-C(O)-Et] | 78 |
| 9 | 1,1'-methylene-bis(5,5-dimethylhydantoin) | 2-ethyloxazoline | {CH2-[hydantoin-N-CH2CH2-NH-C(O)-Et]}2 | 75 |

Examples 1-3 demonstrates the selective nature of the process of the present invention when using a hydantoin reactant having two available —NH sites, in that the reaction occurs selectively at the imide nitrogen.

EXAMPLE 10

The product of Example 9 (232.3 g, 0.50 mole) and 83.3 ml of concentrated HCl in 500 ml of water are placed in a 2-liter flask equipped with means for condensing, heating, and stirring. The mixture is heated to reflux, 100° C., with stirring. It is maintained at reflux with stirring for 12 hours. Water and propionic acid are then removed under reduced pressure. The resulting diethylamine hydrochloride salt is washed with 100 ml of methanol, and is dried. The yield is 80 percent, and the melting point of the diamine salt is 272° C.-275° C.

The diamine hydrochloride salt is dissolved in water and 2 equivalents of NaOH are added to the solution. The water is removed under reduced pressure and the free amine, 1,1'-methylene-bis (3-N-(2-aminoethyl)-5,5-dimethylhydantoin), is dissolved in methanol to precipitate NaCl. The methanol is then removed under reduced pressure to give a 100 percent yield of the diamine, which has a melting point of 103° C.

The structures of compounds formed in this example are confirmed by proton nuclear magnetic resonance spectroscopy.

What is claimed is:
1. A compound having the formula:

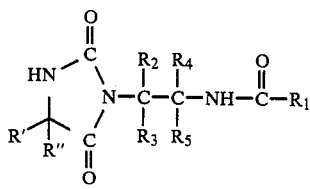

wherein R' and R" are each independently a hydrogen atom or a lower alkyl radical containing up to 6 carbon atoms and $R_1$-$R_5$ are each independently hydrogen or a straight-chain aliphatic radical of 1-12 carbon atoms.

2. A compound of claim 1 wherein R" and R' are hydrogen or methyl, $R_1$ is ethyl and $R_2$ to $R_5$ are each hydrogen.

* * * * *